United States Patent
Sorensen et al.

(10) Patent No.: US 10,639,223 B2
(45) Date of Patent: May 5, 2020

(54) DENTAL INSTRUMENT BRIDGE WITH NOVEL DISPLAY

(71) Applicant: XO Care A/S, Horsholm (DK)

(72) Inventors: Leif K. Sorensen, Klampenborg (DK); Peter V. Sorensen, Horsholm (DK); Torben Hansen, Copenhagen N (DK); Michael G. Nielsen, Copenhagen S (DK); Tom Kristensen, Hellerup (DK); Rasmus Bunkenborg, Copenhagen NV (DK)

(73) Assignee: XO CARE A/S, Horsholm (DK)

( * ) Notice: Subject to any disclaimer, the term of this patent is extended or adjusted under 35 U.S.C. 154(b) by 0 days.

(21) Appl. No.: 16/074,909

(22) PCT Filed: Feb. 3, 2017

(86) PCT No.: PCT/EP2017/052401
§ 371 (c)(1),
(2) Date: Aug. 2, 2018

(87) PCT Pub. No.: WO2017/134236
PCT Pub. Date: Aug. 10, 2017

(65) Prior Publication Data
US 2019/0038494 A1 Feb. 7, 2019

(30) Foreign Application Priority Data
Feb. 3, 2016 (EP) ..................... 16154119

(51) Int. Cl.
*A61G 15/00* (2006.01)
*A61G 15/16* (2006.01)
*A61G 15/14* (2006.01)
*A61B 50/22* (2016.01)

(52) U.S. Cl.
CPC ............. *A61G 15/16* (2013.01); *A61G 15/14* (2013.01); *A61B 50/22* (2016.02)

(58) Field of Classification Search
CPC ........ A61G 15/16; A61G 15/14; A61B 50/22; A61B 50/24
See application file for complete search history.

(56) References Cited

U.S. PATENT DOCUMENTS

| | | | |
|---|---|---|---|
| 5,211,558 A | 5/1993 | Bailey et al. | |
| 7,455,520 B2 * | 11/2008 | Sorensen | A61C 1/0023 433/101 |

(Continued)

FOREIGN PATENT DOCUMENTS

| | | |
|---|---|---|
| EP | 391967 A1 | 10/1990 |
| WO | 89/05613 A1 | 6/1989 |

(Continued)

*Primary Examiner* — Nicholas D Lucchesi
(74) *Attorney, Agent, or Firm* — Fox Rothschild LLP; Carol E. Thorstad-Forsyth

(57) ABSTRACT

Disclosed is a dental instrument bridge for holding a plurality of dental instruments. The dental instrument bridge comprises: a instrument holder configured to hold at least a first dental instrument; and a display for displaying information related to a dental treatment. The display has a first covered portion. The first covered portion being at least partly covered for a user when the first instrument is arranged in the instrument holder.

17 Claims, 5 Drawing Sheets

(56) References Cited

U.S. PATENT DOCUMENTS

| | | | |
|---|---|---|---|
| 8,219,239 B2* | 7/2012 | Andell | A61C 1/0007 433/101 |
| 10,095,650 B2* | 10/2018 | Williams | H04L 12/40 |
| 2006/0046226 A1* | 3/2006 | Bergler | A61G 15/16 433/29 |
| 2009/0166306 A1* | 7/2009 | Ahearn | A61G 15/16 211/85.13 |
| 2014/0378952 A1 | 12/2014 | Humayun et al. | |
| 2015/0359670 A1 | 12/2015 | Lucke | |
| 2019/0070055 A1* | 3/2019 | Sato | A61B 90/90 |

FOREIGN PATENT DOCUMENTS

| | | |
|---|---|---|
| WO | 2004/080324 A1 | 9/2004 |
| WO | 2005/070366 A1 | 8/2005 |

* cited by examiner

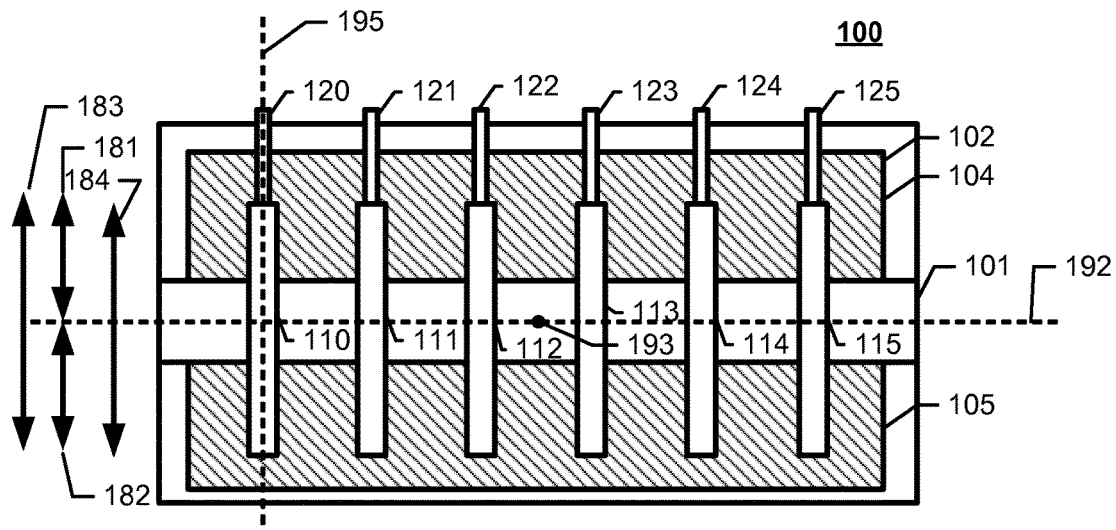
Fig. 1a
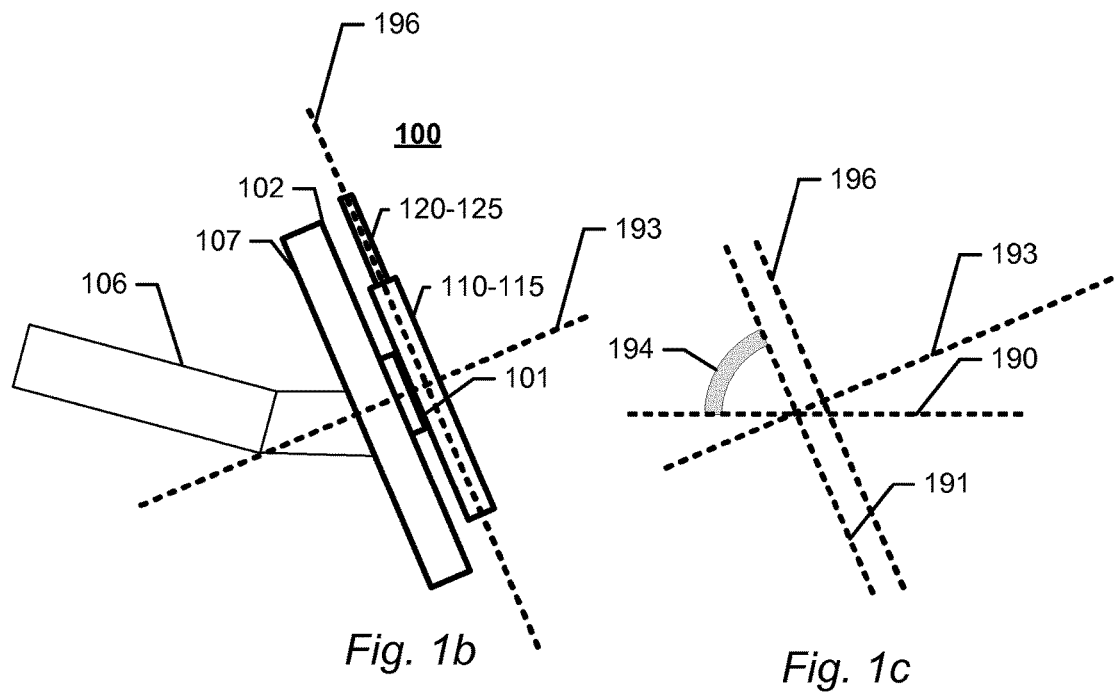
Fig. 1b
Fig. 1c

DENTAL INSTRUMENT BRIDGE WITH NOVEL DISPLAY

CROSS-REFERENCE TO RELATED APPLICATIONS

This application is s U.S. national phase application of PCT International Application No. PCT/EP2017/052401 filed Feb. 3, 2017, which claims priority to European Patent Application No. 16154119.8 filed Feb. 3, 2016. The contents of these applications are incorporated herein by reference in their entirety.

FIELD

The present invention relates to a dental instrument bridge for holding a plurality of dental instruments.

BACKGROUND

Dental examinations and dental treatments require dentists and dental care professionals to perform a number repetitive task. This may lead to various work related injuries. Especially handling of dental instruments such as micro motors, syringes, and curing lights may be problematic. The most commonly used dental instruments are normally arranged on an instrument holder of a movable dental instrument bridge. The dental instrument bridge typically further comprises a display unit for displaying values of control parameters of the plurality of dental instruments and an input unit for setting the values. The input unit may be provided separate from the display or integrated with the display, i.e. the display may be a touch screen.

However, the display unit is normally limited to having a relative small size as the overall size needed by the dental instrument bridge otherwise would make it difficult to arrange it at a desired position. This may make it difficult for a dentist or a dental care professional to view the display and prepare the dental instruments for use. The positioning of the input unit may further force dentist or the dental care professional to make un-ergonomic movements to selected desired values of the control parameters.

WO2004080324 discloses a dental instrument bridge where a small display is arranged next to each dental instrument.

Thus, it remains a problem to provide a dental instrument bridge that is easier to operate and provides a more ergonomic work environment for dentists and dental care professionals.

SUMMARY

According to a first aspect, the invention relates to a dental instrument bridge for holding a plurality of dental instruments, said dental instrument bridge comprising:
- an instrument holder configured to hold at least a first dental instrument; and
- a display for displaying information related to a dental treatment;
- wherein in said display has a first covered portion said first covered portion being at least partly covered for a user when said first instrument is arranged in said instrument holder and wherein said display is capable of displaying information related to a dental treatment in said first covered portion.

Consequently, by integrating a display in the dental instrument bridge a larger display may be used without increasing the required space of the dental instrument bridge thereby providing a more ergonomic dental instrument bridge.

The display may be any display such as a Light-emitting diode display (LED), Electroluminescent display (ELD), Cathode ray tube display (CRT), Plasma display panel (PDP), Liquid crystal display (LCD), High-Performance Addressing display (HPA), Thin-film transistor display (TFT), Organic light-emitting diode display (OLED), Surface-conduction electron-emitter display (SED), or Field emission display (FED). The instrument holder may be configured to hold the first dental instrument in front of the display so that the portion of the display behind the first dental instrument becomes covered when the first dental instrument is arranged in the instrument holder, i.e. the portion of the display behind the first dental instrument will be the first covered portion. The information related to a dental treatment may be a value of one or more control parameters of dental instruments held by the instrument holder, instruction for using the dental instruments, information indicative of the status of the dental instrument or the like.

In some embodiments, said dental instrument bridge is configured to detect when a user selects and picks up said first dental instrument and in response thereto control the display to change the current display and show first information relevant for the use of said first dental instrument.

This allows the display to be adapted to display information specifically relevant for operating the selected instrument.

The dental instrument bridge may comprise a housing wherein the display is arranged in said housing. The dental instrument bridge may comprise a processing unit configured to detect when a user selects and picks up dental instruments and further control the display e.g. the processing unit may be configured to detect when a user selects and picks up the first dental instrument and in response thereto control the display to change the current display and show first information relevant for the use of said first dental instrument. The processing unit may be configured to detect when a user selects and picks up the first dental instrument by receiving a sensor signal from the first dental instrument, the instrument holder and/or from another part of the dental instrument bridge. Alternatively/additionally the dental instrument bridge may be configured to receive control signals from a processing unit arranged in another part of a dental unit which the dental instrument bridge forms part of and/or a processing unit arranged outside the dental unit. The information relevant for the use of the first dental instrument may be the current value(s) of one or more control parameters of the first dental instrument, the name of the first dental instrument, the status of the first dental instrument, the name of a selected program for setting the value(s) of one or more control parameters to a predetermined value. The instrument holder may be configured to hold the first dental instrument approximately at a predetermined position whereby the first dental instrument covers for said first covered portion of the display. The entire display or only a portion of the display may be changed when the first dental instrument is selected. The dental instrument bridge may be configured to provide one or more dental instruments with electrical power, compressed air, a vacuum and/or water. The dental instrument bridge may further be configured to provide one or more dental instruments with control signals for setting values of control parameters. The covered portion(s) of the display may be covered at least when the angle between the visual axis of a user and the central axis of the display is between 0 and 85 degrees, between 0 and 75 degrees, between 0 and 45 degrees, or between 0 and 20 degrees, where the central axis of the display is the axis arranged in the centre of the display and being perpendicular to a first reference plane in which a planar display surface of the display extends. The visual axis of a user is in this disclosure defined as the axis going through the point arranged in the middle between the two eyes of the user and the point arranged in the centre of the display, i.e. when the angle between the central axis of the display and the visual axis of the user is zero degrees the user is arranged right in front of the display.

There will always be two angles between two axes or two planes, a small angle V1 and a large angle V2, where V2=180 degrees−V1. In this disclosure, it will always be the small angle V1 that is specified whenever the angle between two axes or two planes is mentioned. Furthermore, the angle between two non-intersecting parallel axes or planes is 0 degrees, In some embodiments, the first dental instrument is a micro motor (e.g. for a drill), a syringe, a curing light, a camera, an air instrument (turbine), a curing light, a scaler, or intraoral camera.

In some embodiments, the dental instrument bridge further comprises the first dental instrument, the first dental instrument being arranged in the instrument holder whereby the first dental instrument at least partly covers the first covered portion and wherein the first dental instrument is a micro motor (e.g. for a drill), a syringe, a curing light, a camera, an air instrument (turbine), a curing light, a scaler, or an intraoral camera.

In some embodiments, said display has a first adjacent portion being adjacent to said first covered portion, wherein the display is configured to display information relevant for the use of said first dental instrument inside said first adjacent portion.

Consequently, the display may provide relevant information directly in connection with the dental instruments.

The information relevant for the use of said first dental instrument may be values of control parameters for said first dental instrument, the status of the first instrument. The information relevant for the use of said first dental instrument may be permanently displayed or only displayed when said display is in a particular state.

In some embodiments, the information relevant for the use of said first dental instrument may be a visual indicator indicating to the user that the first dental instrument should be used for a next step of a particular dental treatment.

As an example a dental unit, which the dental instrument bridge forms part of, may comprises a plurality of pre-programmed dental treatments where each dental treatment comprises a plurality of steps. Thus, the visual indicator may indicate to the user that the first dental instrument should be used for the next step of a selected pre-programmed dental treatment. The first adjacent portion may have any size e.g. it may have a surface area comparable to the first covered portion or even larger than the first covered portion. Alternatively, the first adjacent portion may have a small size e.g. it may only form a rim around some or all of the first covered portion.

In some embodiments, said instrument holder is configured to hold a plurality of dental instruments; said display has a plurality of covered portions each covered portion of said plurality of covered portions being at least partly covered by one of said plurality of dental instruments when said one of said plurality of dental instruments is arranged in said instrument holder, and wherein said dental instrument bridge is configured to detect when a user selects and picks up a selected dental instrument of said plurality of dental instruments and in response thereto is configured to control the display to change the current display and show information relevant for the use of said selected dental instrument and wherein said display is capable of displaying information related to a dental treatment in said plurality of covered portions.

Consequently, a compact dental instrument bridge capable of holding a plurality of dental instruments and having a large display is provided.

The instrument holder may be configured to hold the plurality of dental instruments approximately at predetermined positions.

In some embodiments, the dental instrument bridge further comprises the plurality of dental instruments, the plurality of dental instruments being arranged in the instruments holder wherein said plurality of dental instruments are selected from the list of dental instruments consisting of:
a micro motor e.g. for a drill;
a syringe;
a curing light:
a camera:
an air instrument (turbine);
a curing light;
a scaler; and
an intraoral camera.

The dental instruments typically comprise a proximal end having a handle allowing the dentist to grip the dental instruments and a distal end for interacting with the mouth of a patient. The instrument holder may be configured to hold the dental instruments in any manner e.g. with the distal end facing downwards or with the distal end facing upwards. The dental instruments may be connected to the dental instrument bridge via a hose configured to provide the dental instruments with electrical power, compressed air, a vacuum and/or water. The dental instrument bridge may comprise a plurality of hose holders for holding hoses connected to the dental instruments, wherein the plurality of hose holders are arranged above the instrument holder.

In some embodiments, the dental instrument bridge further comprises a plurality of dental instruments arranged in the instrument holder.

In some embodiments, said display has an adjacent portion next to each of said plurality of covered portions wherein the display is configured to, for each of said adjacent portions, show information relevant for the use of their respective dental instrument.

In some embodiments, the information relevant for the use of the respective dental instrument is a visual indicator indicating to the user that the respective dental instrument should be used for a next step of a particular dental treatment.

The plurality of adjacent portions may be activated at different points in time e.g. if the information relevant for the use of a dental instrument is a visual indicator indicating to the user that the dental instrument should be used for the next step of a selected pre-programmed dental treatment only one adjacent portion may be activated at a particular point in time (or maybe only two adjacent portions if two instruments are needed for a particular step in a dental treatment). The visual indicator may additionally be displayed at the covered portions of said respective dental instrument and thereby visible to the user after the user has selected the respective dental instrument. The plurality of adjacent portions may have any size e.g. they may have a surface area comparable to the plurality of covered portions or even larger than the plurality of covered portions. Alternatively, the plurality of adjacent portions may have a small size e.g. they may only form a rim around some or all of their respective covered portion.

In some embodiments, the first information relevant for the use of said selected dental instrument are displayed outside said plurality of covered portions and/or inside said covered portion of said selected dental instrument.

Consequently, the dental instrument bridge may in effective manner use the non-covered parts of the display, i.e. when a dental instrument is selected the dental instrument bridge knows which parts of the display is visible and may display the relevant information in theses visible parts.

In some embodiments, the information relevant for the use of said selected dental instrument comprises value(s) of one or more control parameters of said selected dental instrument, and wherein said value(s) of said one or more control parameters are displayed outside said plurality of covered portions or inside said covered portion of said selected dental instrument.

Examples of control parameters for a micro motor are: speed (RPM), torque (%), spray water (ml/min), spray air (%), direction of rotation (forward/backwards). Examples of control parameters for a curing light are: state (on/off), time on (seconds), intensity (lumen). Examples of control parameter for an air instrument are: state (on/off), air flow (%), spray water (ml/min).

In some embodiments, said dental instrument bridge is configured to in response to receiving a first control signal change the display of said screen whereby second information relevant for the use said selected dental instrument is displayed.

In some embodiments, said instrument holder comprises an elongated member extending along a central longitudinal axis.

The central longitudinal axis being the central longitudinal axis of the elongated member.

In some embodiments, said display comprises a first elongated part extending along said central longitudinal axis below or above said elongated member of said instrument holder.

In some embodiments, said first elongated part extends along said central longitudinal axis below said elongated member of said instrument holder; said display further comprises a second elongated part extending along said central longitudinal axis above said elongated member of said instrument holder.

By having a screen with a first and a second part, the elongated member of the instrument holder may be arranged in the middle of screen. This allows the screen to use most of the space normally only occupied by the instruments.

In some embodiments, the elongated member comprises a plurality of concave portions, each concave portion being configured to hold a dental instrument.

Consequently, an easy way to secure that the plurality of dental instruments are being held at approximately predetermined positions is provided.

In some embodiments, the dental instrument bridge further comprises a housing and a movable arm, said display is arranged in said housing and said movable arm is connected to said housing, wherein said movable arm is configured to allow a user to arranged said instrument bridge at a desired position with respect to a patient.

In some embodiments, said dental instrument bridge further comprises a handle protruding from said housing.

In some embodiments, said display has a planar display surface extending in a first reference plane being angled with respect to the horizontal plane with an angle between 10 and 90 degrees, between 25 and 90 degrees, or between 35 and 80 degrees.

In some embodiments, said display has a planar display surface extending in a first reference plane, the first dental instrument is an elongated dental instrument extending along a first central longitudinal axis, and the instrument holder being configured to hold the first dental instrument in a manner whereby the angle between the first central longitudinal axis and the first reference plane is less than 30, 20, or 10 degrees.

This allows the display to more effectively use the dead space occupied by the first instrument. The first central longitudinal axis being the central longitudinal axis of the first dental instrument.

The first central longitudinal axis is preferably parallel with the first reference plane i.e. the angle between the first central longitudinal axis and the first reference plane is preferably 0 degrees.

In some embodiments, the planar display surface of the display has a length along the first central longitudinal axis of at least 5 cm, 10 cm, or 15 cm.

If the display comprises a plurality of parts, then the length of the display surface along the first central longitudinal axis is defined as the sum of the length of the display surface of each part along the first central longitudinal axis.

In some embodiments, the planar display surface of the display has a length along the first central longitudinal axis of at least 25%, 50%, or 75% of the length of the first dental instrument along the first central longitudinal axis.

In some embodiments, the plurality of dental instruments are elongated dental instruments extending along central longitudinal axes, the instrument holder being configured to hold the plurality of dental instruments in a manner whereby their central longitudinal axes are arranged a third reference plane, the angle between the third reference plane and the first reference plane is less than 30, 20, or 10 degrees.

The third reference plane is preferably parallel with the first reference plane i.e. the angle between the first reference plane and the third reference plane is preferably 0 degrees. The instrument holder is preferably further configured to hold the plurality of dental instruments in a manner whereby their central longitudinal axes are parallel.

In some embodiments, the planar display surface of the display has a length along the central longitudinal axes of at least 25%, 50%, or 75% of the average length of the plurality of dental instruments along the central longitudinal axes.

The instrument holder may be configured to hold the plurality of dental instruments so that the maximum distance from any one of the plurality of dental instruments to the display is no more than 12 cm, no more than 8 cm, or no more than 4 cm.

In some embodiments, said dental instrument bridge further comprises an input unit for controlling functionalities of dental equipment, wherein said instrument holder comprises an elongated member extending along a central longitudinal axis, said elongated member being configured to hold the first dental instrument, a second dental instrument and a third dental instrument at three approximately predetermined positions; the display having a second covered portion and a third covered portion the second covered portion being at least partly covered when said second instrument is arranged in said instrument holder and said third covered portion being at least partly covered when said third dental instrument is arranged in said instrument holder; and said input unit comprises an elongated input zone configured to allow a user to control functionalities of dental equipment using an object such as a finger wherein said elongated input zone is arranged above or below said elongated member in manner and having a width along said central longitudinal axis whereby a user may select any one of said first, second or third dental instruments with a first hand and directly with said first hand enter said elongated input zone without moving said first hand along said central longitudinal axis.

Consequently, an ergonomic input unit is provided allowing the dentist to select any dental instrument and in a natural movement directly enter the elongated input zone.

The elongated input zone may comprise one or more buttons and/or an elongated trackpad. The elongated trackpad may be a 1 dimensional trackpad, i.e. a slider or a 2 dimensional trackpad. The functionalities of dental equipment may be values of one or more control parameters for the first, second and third dental instrument. Additionally/alternatively the functionalities of dental equipment may be values of control parameters of other parts of a dental unit which the dental instrument bridge forms part of e.g. the elongated input zone may be configured to allow a user to control the position of a dental chair, the light source of a dental light or the like. The dental instrument bridge may be configured to change the functionality of the elongated input zone in response to a user selects and picks up a dental instrument so that the elongated input zone may be used for setting values of one or more control parameters for the selected dental instrument. The elongated input zone may be a touch screen. The touch screen may be a separate screen separate from the display of the dental instrument bridge. Alternatively the touch screen may also constitute the display of the dental instrument bridge.

In some embodiments, the display has one or more input unit portions, wherein the dental instrument bridge is configured to control the display to show information indicating the functionality of the elongated input zone at the one or more input unit portions.

In some embodiments, said elongated input zone comprises at least three buttons for controlling functionalities of dental equipment such as setting values of one or more control parameters for each of said first, second or third dental instrument.

In some embodiments, said elongated input zone comprises a planar surface extending in a second reference plane and at least three buttons for setting values of one or more control parameters for each of said first, second or third dental instrument.

The elongated input zone may comprise more than 3 buttons e.g. at least 4, 5, 6 or 7 buttons.

In some embodiments said at least three buttons are proximity buttons configured to detect the presence of an object without any physical contact between said object and said proximity button and in response thereto generate an activation signal.

The object may be the finger of a user, a pen, or a part of a dental instrument. The proximity buttons may be configured to emit an electromagnetic field or a beam of electromagnetic radiation such as infrared radiation, and looks for changes in the field or return signal. The proximity buttons may use capacitive sensing to detect the presence of the object without any physical contact between the object and said proximity buttons.

In some embodiments, the centre of each of said at least three buttons are arranged with a distance along said central longitudinal axis to any one of said three covered portions of said display whereby the parts of the display arranged immediately above or below said buttons are freely visible also when all dental instruments are arranged in the instrument holder.

In some embodiments, said display has at least three input unit portions in the form of three button portions one arranged above/below said first button, one arranged above/below said second button and one arranged above/below said third button, wherein the dental instrument bridge is configured to control the display to display information indicating the functionality of the at least three buttons in their respective button portions of the display.

Consequently, the user may in an easy manner perceive the functionality of the three buttons thereby improving the user friendliness.

The display may be operatively connected to a processing unit, whereby the display may be configured to display particular information at particular locations in particular states by receiving control signals from said processing unit.

According to a second aspect the invention relates to a dental unit for dental treatments comprising:
  a dental instrument bridge as disclosed in relation to the first aspect of the invention; and
  a patient chair.

According to a third aspect, the invention relates to a dental instrument bridge for holding a plurality of dental instruments, said dental instrument bridge comprising:
  an instrument holder configured to hold at least a first dental instrument; and
  a display for displaying information related to a dental treatment;
  wherein said display has a planar display surface extending in a first reference plane being angled with respect to the horizontal plane with an angle between 10 and 90 degrees, the first dental instrument is an elongated dental instrument extending along a first central longitudinal axis, and the instrument holder being configured to hold the first dental instrument in a manner whereby the angle between the first central longitudinal axis and the first reference plane is less than 30 degrees and the planar display surface of the display has a length along the first central longitudinal axis of at least 25% of the length of the first dental instrument along the first central longitudinal axis.

The different aspects of the present invention can be implemented in different ways including as a dental instrument bridge, and a dental unit comprising a dental instrument bridge described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependant claims. Furthermore, it will be appreciated that embodiments described in connection with one of the aspects described herein may equally be applied to the other aspects. Especially, embodiments disclosed in relation to the first aspect of the invention may be applied to the third aspect of the invention.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 1a-e show a dental instrument bridge according to an embodiment of the present invention.

DETAILED DESCRIPTION

In the following description, reference is made to the accompanying figures, which show by way of illustration how the invention may be practiced.

Figure 1D:
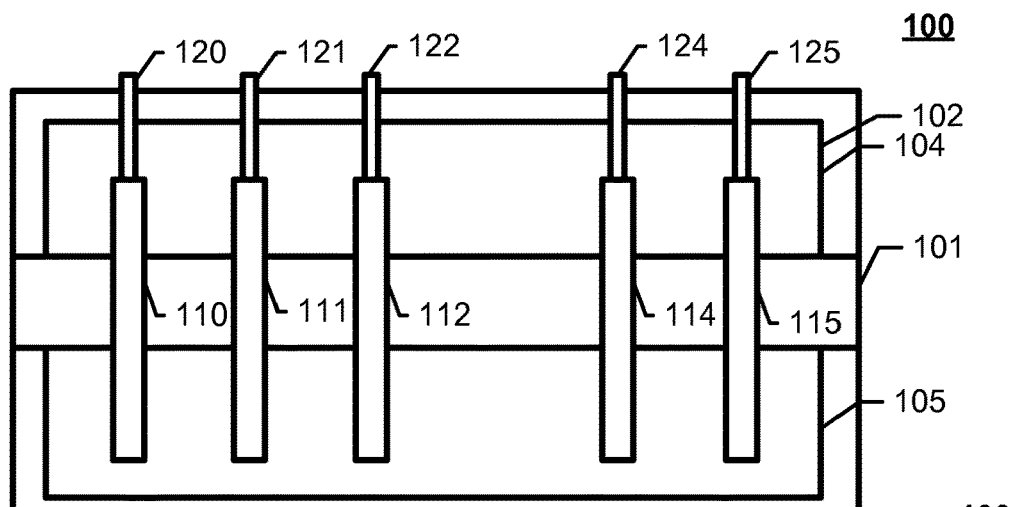
Figure 1E:
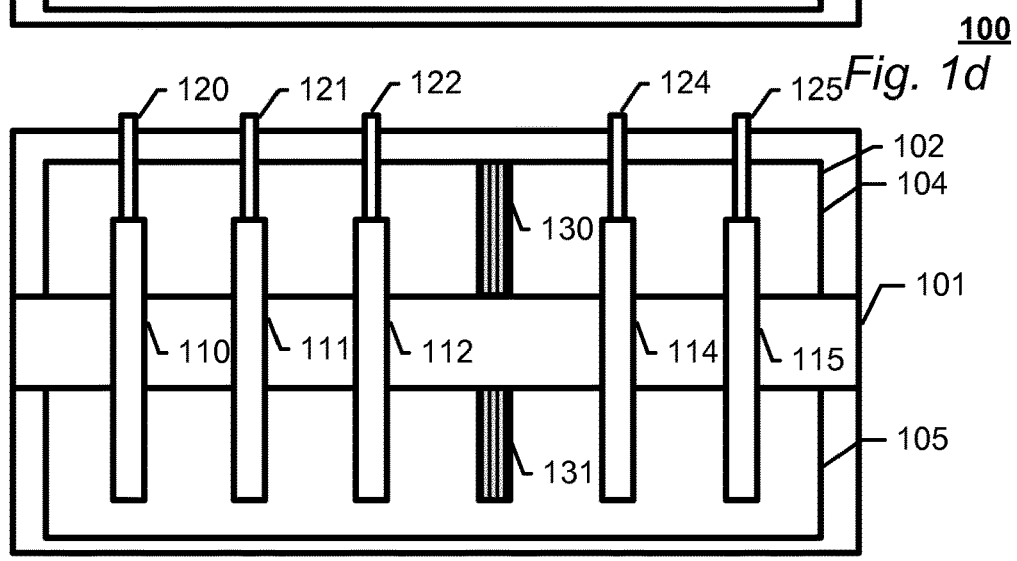

FIGS. 1a-e show a dental instrument bridge 100 according to an embodiment of the present invention, where FIGS. 1a,1d and 1e show a front view and FIGS. 1b-c show a side view. The dental instrument bridge 100 is configured to hold a plurality of dental instruments 110-115. In this embodiment the dental instrument bridge is configured to hold six dental instruments but in other embodiments the dental instrument bridge may be configured to hold at least 1, 2, 3, 4, 5 or 6 dental instruments. The dental instrument bridge 100 comprises an instrument holder 101 and a display 102 for displaying values of one or more control parameters of one or more of the six dental instruments 110-115. The instrument holder 101 is configured to hold the six dental instruments 110-115. Each of the six dental instruments 110-115 are connected to a hose 120-125. The dental instrument bridge 100 is configured to provide the dental instruments 110-115 with electrical power, compressed air, a vacuum, water, and/or control signals for setting values of control parameters through the hoses 120-125. The instrument holder 101 may be configured to secure the dental instruments at their respective resting positions, i.e. the instrument holder may be configured to grip each of the dental instruments 110-115. Alternatively/additionally the dental instruments 110-115 may be at least partly held by the hoses 120-125. The instrument holder 101 comprises an elongated member extending along a central longitudinal axis 192. The dental instruments 110-115 are arranged in front of the display so that each dental instrument 110-115 cover of a portion of the display 102 when the dental instrument 110-115 is arranged on the instrument holder 101. The display 102 has a planar display surface that extends in a first reference plane 191 being angled with respect to the horizontal plane 190 with an angle 194. Each dental instrument 110-115 covers a portion of the display 102 at least when the angle between the visual axis of the user and the central axis of the display 193 is between 0 and 85 degrees, between 0 and 75 degrees, between 0 and 45 degrees, or between 0 and 20 degrees, where the central axis of the display 193 is the axis arranged in the centre of the display 102 and being perpendicular to the first reference plane 191 in which the planar display surface of the display 102 extends.

The dental instruments 110-115 are elongated dental instruments extending along central longitudinal axes (only the axis 195 for the dental instrument 110 is shown), the instrument holder 101 being configured to hold the plurality of dental instruments 110-115 in a manner whereby their central longitudinal axes are arranged in a third reference plane 196 and the angle between the third reference plane 196 and the first reference plane 191 is less than 20 degrees. This secures that the dead space behind the dental instruments 110-115 is effectively used by the display 102. In this embodiment the first reference plane 191 and the third reference plane 196 are parallel thus the angle between them is 0 degrees.

In this embodiment, the planar display surface of the display 102 has a length along the first central longitudinal axis 183 substantially corresponding to the the average length 184 of the plurality of dental instrument 110-115 along their central longitudinal axis, i.e. the planar display surface of the display 102 has a length along the first central longitudinal axis 183 of at least 75% of the average length 184 of the plurality of dental instrument 110-115 along their central longitudinal axis.

The display comprises two parts 104 105. Thus, as mentioned previously, the length of the planar display surface along the central longitudinal axes 183 is defined as the sum of the length of the display surface of each part 181 182 along the central longitudinal axes.

The dental instrument bridge 100 is configured to detect when a user selects and picks up one of the six dental instruments 110-115 and in response thereto control the display to change the current display and show first information relevant for the use of the selected dental instrument. Consequently, by integrating a display in the dental instrument bridge 100 a larger display may be used without increasing the required space of the dental instrument bridge thereby providing a more ergonomic dental instrument bridge.

The dental instrument bridge 100 further comprises a housing 107 connected to a movable arm 106. The display 102 is arranged in the housing 107. The movable arm is configured to allow a user to arrange the dental instrument bridge 100 at a desired position. The display 102 comprises a first elongated part 104 extending along the central longitudinal axis 192 above the elongated member of the instrument holder 101 and a second elongated part 105 extending along the central longitudinal axis 192 below said elongated member of the instrument holder. The first elongated part 104 and the second elongated part 105 may be parts of one large single display, i.e. the elongated member of the instrument holder 101 may permanently cover a part of the display 102 thereby dividing the single display into an upper part and a lower part. Alternatively, the first elongated part 104 may be a first display and the second elongated part 105 may be a second display, where the first and the second display together forms the display 102 of the dental instrument bridge 100.

FIG. 1d shows the dental instrument bridge 100 after a user has selected and picked up the dental instrument 113, and FIG. 1e shows the portion of the display 130 131 being covered by the dental instrument 113, when the dental instrument 113 is arranged in the instrument holder 101. At least a part of the portion of the display 130 131 may preferably be used for displaying information relevant for the use of the dental instrument 113.

Figure 2A:
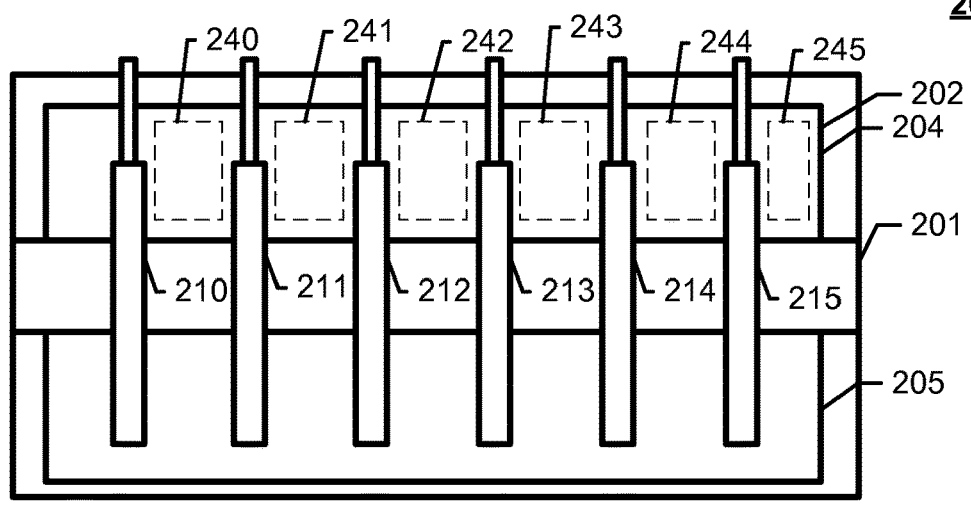
FIGS. 2a-b show a dental instrument bridge according to an embodiment of the present invention.
Figure 2B:
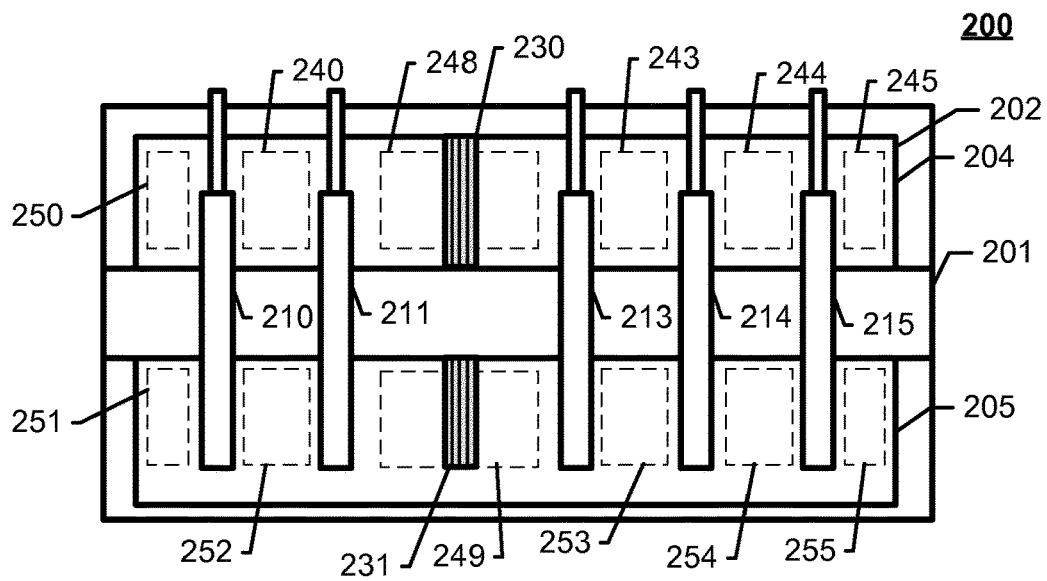

FIGS. 2a-b show dental instrument bridge 200 according to an embodiment of the present invention. The dental instrument bridge 200 is configured to hold a plurality of dental instruments 210-215. The dental instrument bridge 200 comprises an instrument holder 201 and a display 202 for displaying values of one or more control parameters of one or more of the six dental instruments 210-215. The instrument holder 201 is configured to hold the six dental instruments 210-215. Each of the six dental instruments 210-215 are connected to a hose. The instrument holder 201 comprises an elongated member extending along a central longitudinal axis. The dental instruments 210-215 are arranged in front of the display so that each dental instrument 210-215 cover a portion of the display 202 when the dental instrument is arranged on the instrument holder 201. The display 202 comprises a first elongated part 204 extending along the central longitudinal axis above the elongated member of the instrument holder 201 and a second elongated part 205 extending along the central longitudinal axis below said elongated member of the instrument holder 201. FIG. 2a shows how the display may look when none of the dental instrument 210-215 has been selected. The display comprises six covered portions each covered portion being covered by one of the six dental instruments 210-215 when the dental instruments 210-215 are arranged in the instrument holder 201. The display 202 further has adjacent portions 240-245 next to each of the plurality of covered portions, and the display is configured to show information relevant for the use of the plurality of dental instruments at their respective adjacent portions. Thus the display shows information relevant for the use of the dental instrument 210 at the adjacent portion 240, information relevant for the use of the dental instrument 211 at the adjacent portion 241, information relevant for the use of the dental instrument 212 at the adjacent portion 242, information relevant for the use of the dental instrument 213 at the adjacent portion 243, relevant for the use of the dental instrument 214 at the adjacent portion 244, and information relevant for the use of the dental instrument 215 at the adjacent portion 245. The information relevant for the use of the dental instruments may be information descriptive of the dental instruments 210-215 such as information descriptive of: the instrument type or the instrument status e.g. current control parameter values or the name of a selected program for setting the value(s) of one or more control parameters to a predetermined value. The dental instrument bridge may be configured to automatically determine the information descriptive of the dental instruments. Additionally/alternatively the information relevant for the use of a dental instrument may be a visual indicator indicating to the user that the dental instrument should be used for the next step of a selected pre-programmed dental treatment e.g. for the first step of the selected pre-programmed dental treatment the adjacent portion 241 may be activated and indicate to the user that the dental instrument 211 should be used for the first step, for the second step the adjacent portion 244 may be activated and indicate to the user that the dental instrument 214 should be used for the second step, and so forth. FIG. 2b shows how the display 202 may look after a user have selected and picked up the dental instrument 212. Shown is the portion of the display 230 231 covered by the dental instrument 212 when the dental instrument is arranged on the instrument holder 201. The dental instrument bridge 200 is in this state configured to display information relevant for the use of the dental instrument 212 outside the plurality of covered portions or inside the covered portion 230 231 of the selected dental instrument. As an example, if the dental instrument 212 is a micro motor e.g. having a dental drill attached, the portion of the display 252 may show the speed of the micro motor (RPM), the portion of the display 253 may show the torque (%), the portion of the display 254 may show spray water (ml/min), the portion of the display 248 may show the type of micro motor, e.g. its product name or product number, and the portion of the display 249 may display the type of dental drill e.g. its product name or product number.

The dental instrument bridge 200 may be configured to automatically detect which dental instruments 210-215 are arranged in the instrument holder 201 and where on the instrument holder 201 they are arranged and in response thereto configure the display 202 accordingly. This allows a user to select any desired dental instruments and arrange the selected dental instruments in any desired custom order. As an example if the user exchanges the position of the dental instruments 211 and 213 the dental instrument bridge 200 may automatically detect the new positions of dental instruments 211 and 213 and in response thereto change adjacent portion 241 to display information relevant for the use of the dental instrument 213 and change adjacent portion 243 to display information relevant for the use of the dental instrument 211. The dental instrument bridge 200 may be configured to detect which dental instruments are arranged in the instrument holder 201 and where on the instrument holder 201 they are arranged by having one or more sensors arranged in or in connection with the dental instrument bridge 200. Additionally/alternatively the dental instrument bridge 200 may comprise a plurality of connection ports for connecting the dental instruments 210-215 to the dental instrument bridge 200 via a connection member such as an instrument hose, wherein each connection port is provided in connection with an approximately predetermined instrument holding position e.g. a particular concave portion of the instrument holder as shown in relation to FIGS. 5-8, whereby the dental instrument bridge 200 may be able to detect which dental instruments are arranged in the instrument holder 201 and where on the instrument holder 201 they are arranged by receiving data from the instruments through the connection ports.

Figure 3:
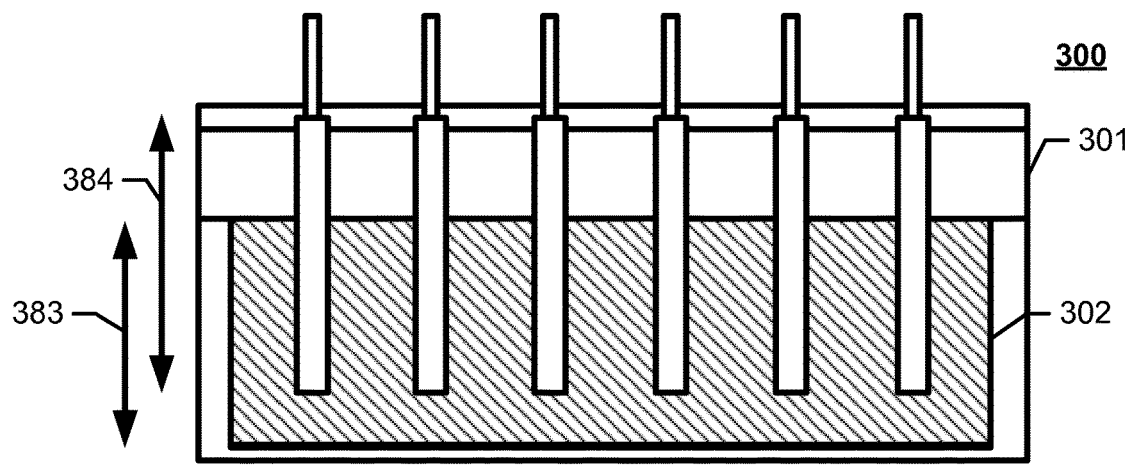
FIG. 3 shows a dental instrument bridge according to an embodiment of the present invention.

FIG. 3 shows a dental instrument bridge according to an embodiment of the present invention. This embodiment is similar to the embodiment shown in FIG. 1 with the difference that the display 302 only comprises a single elongated part arranged below the elongated member of the instrument holder 301. The display 302 has a planar display surface extending in a first reference plane. The plurality of dental instruments are elongated dental instruments extending along parallel central longitudinal axes, the instrument holder 301 being configured to hold the plurality of dental instruments in a manner whereby their central longitudinal axes are parallel and arranged in a third reference plane the angle between the third reference plane and the first reference plane is less than 20 degrees. The planar display surface of the display 302 has a length 383 along the central longitudinal axes of at least 75% of the average length of the plurality of dental instruments 384 along the central longitudinal axes.

Figure 4:
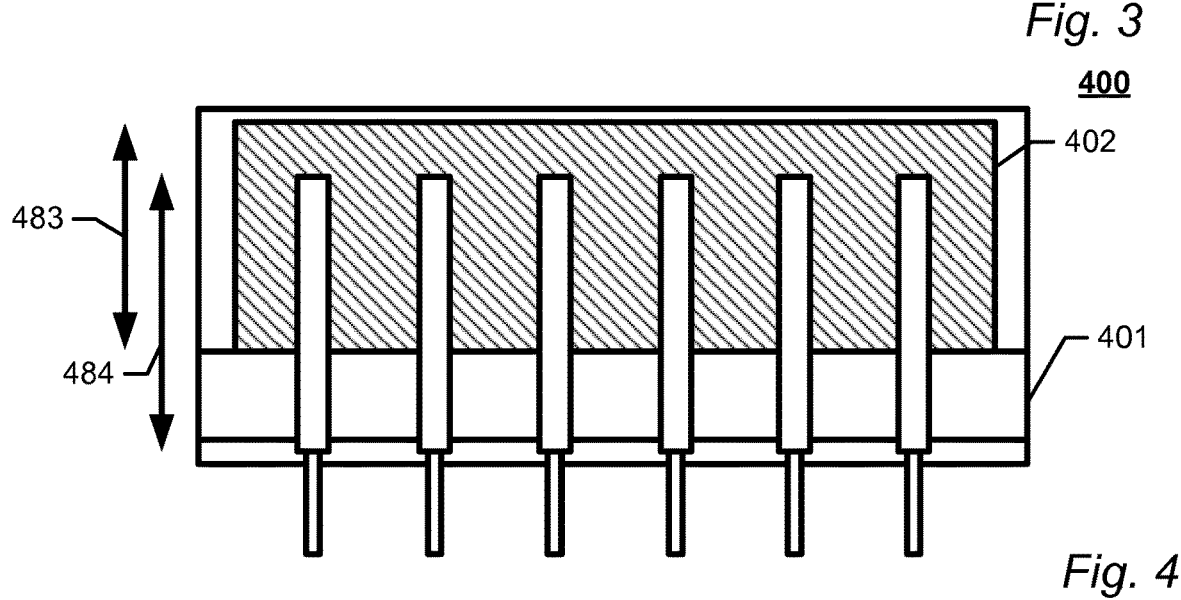
FIG. 4 shows a dental instrument bridge according to an embodiment of the present invention.

FIG. 4 shows a dental instrument bridge according to an embodiment of the present invention. This embodiment is similar to the embodiment shown in FIG. 3 with the difference that the single elongated part of the display 402 is arranged above the elongated member of the instrument holder 401 and the instrument holder 401 is configured to hold the dental instruments in a manner so that the distal ends of the dental instruments are pointing in an upwards direction. The display 402 has a planar display surface extending in a first reference plane. The plurality of dental instruments are elongated dental instruments extending along parallel central longitudinal axes, the instrument holder 401 being configured to hold the plurality of dental instruments in a manner whereby their central longitudinal axes are parallel and arranged in a third reference plane the angle between the third reference plane and the first reference plane is less than 20 degrees. The planar display surface of the display 402 has a length 483 along the central longitudinal axes of at least 75% of the average length of the plurality of dental instruments 484 along the central longitudinal axes.

Figure 5:
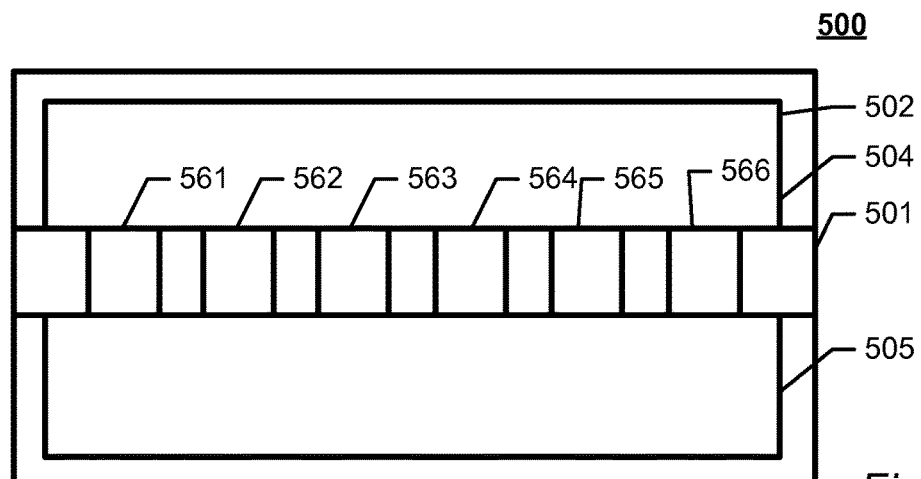
FIG. 5 shows a dental instrument bridge according to an embodiment of the present invention.

FIG. 5 shows a dental instrument bridge 500 according to an embodiment of the present invention. The dental instrument bridge comprises: an instrument holder 501 configured to hold a plurality of dental instruments and a display 502 for displaying values of one or more control parameters of the plurality of dental instruments. The instrument holder 501 comprises an elongated member extending along a central longitudinal axis and the display 502 comprises a first elongated part 504 arranged above the elongated member of the instrument holder 501 and a second elongated part 505 arranged below the elongated member of the instrument holder 501. In this embodiment the elongated member of the instrument holder 501 comprises six concave portions 561-566, each concave portion being configured to hold a dental instrument.

Figure 6:
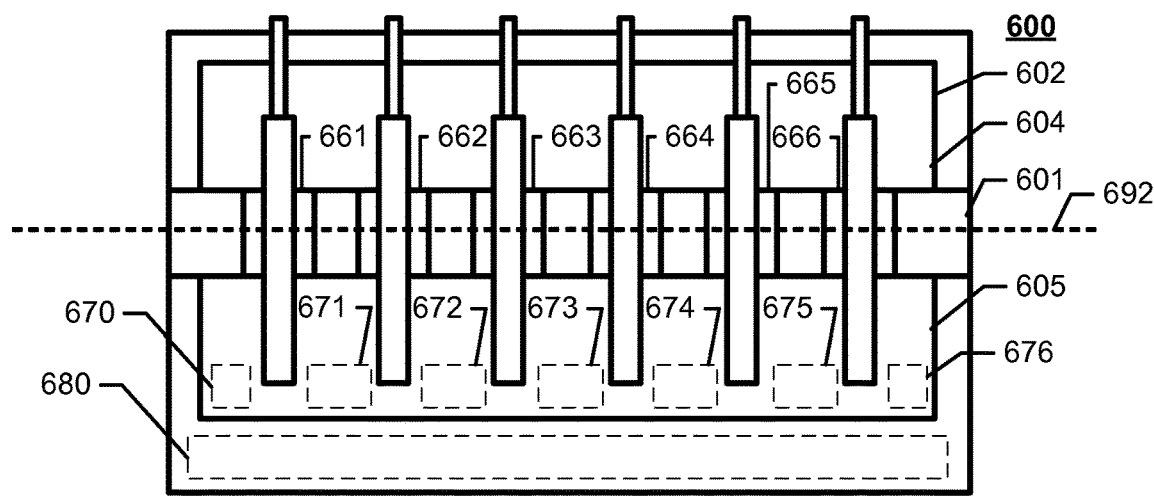
FIG. 6 shows a dental instrument bridge according to an embodiment of the present invention.

FIG. 6 shows a dental instrument bridge 600 according to an embodiment of the present invention. The dental instrument bridge 600 comprises: an instrument holder 601 configured to hold a plurality of dental instruments and a display 602 for displaying values of one or more control parameters of the plurality of dental instruments. The instrument holder 601 comprises an elongated member extending along a central longitudinal axis 692 and the display 602 comprises a first elongated part 604 arranged above the elongated member of the instrument holder 601 and a second elongated part 605 arranged below the elongated member of the instrument holder 601. The elongated member of the instrument holder 601 comprises six concave portions 661-666, each concave portion holding a dental instrument. In this embodiment the dental instrument bridge 600 further comprises an input unit for setting values of one or more control parameters for one or more of the dental instruments. The input unit comprises an elongated input zone 680 configured to allow a user to select values of one or more control parameters for the dental instruments using a finger. The elongated input zone 680 is arranged below said elongated member of the instrument holder 601 in manner and having a width along the central longitudinal axis 692 whereby a user may select any one of the six dental instruments with a first hand and directly with the first hand enter the elongated input zone 680 without moving the first hand along the central longitudinal axis 692. Thus, an ergonomic input unit is provided allowing the dentist to select any dental instrument and in a natural movement directly enter the elongated input zone 680. The elongated input zone 680 may comprises a plurality of buttons and/or an elongated trackpad. The display 602 has seven input unit portions 670-676. The dental instrument bridge 600 is configured to control the display 602 to show information indicating the functionality of the elongated input zone 680 at one or more of the seven input unit portions 670-676.

Figure 7A:
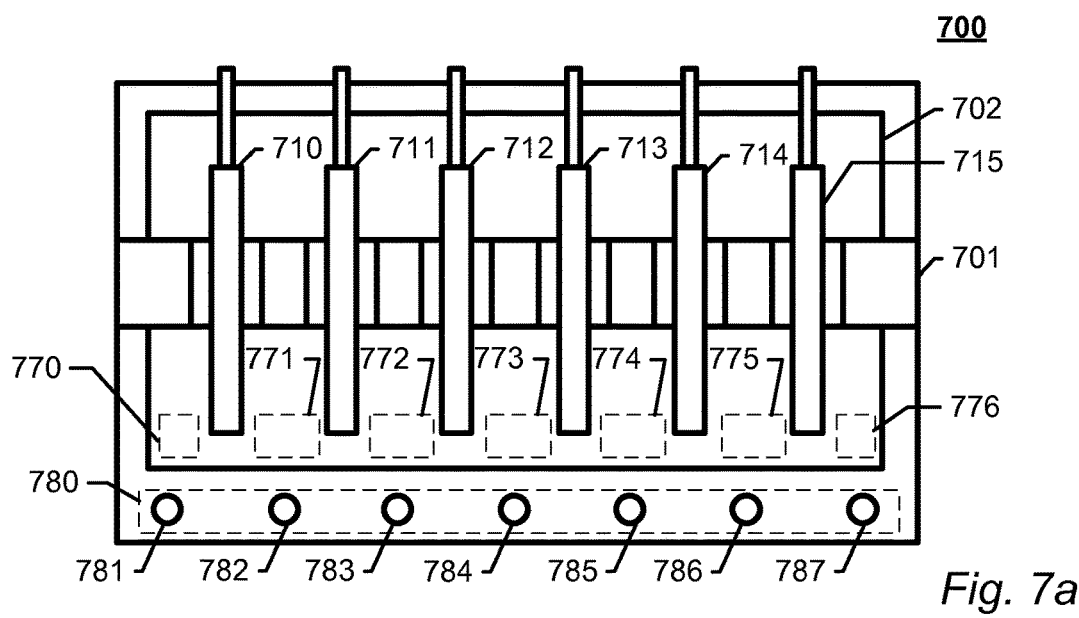
FIGS. 7a-b show a dental instrument bridge according to an embodiment of the present invention.
Figure 7B:
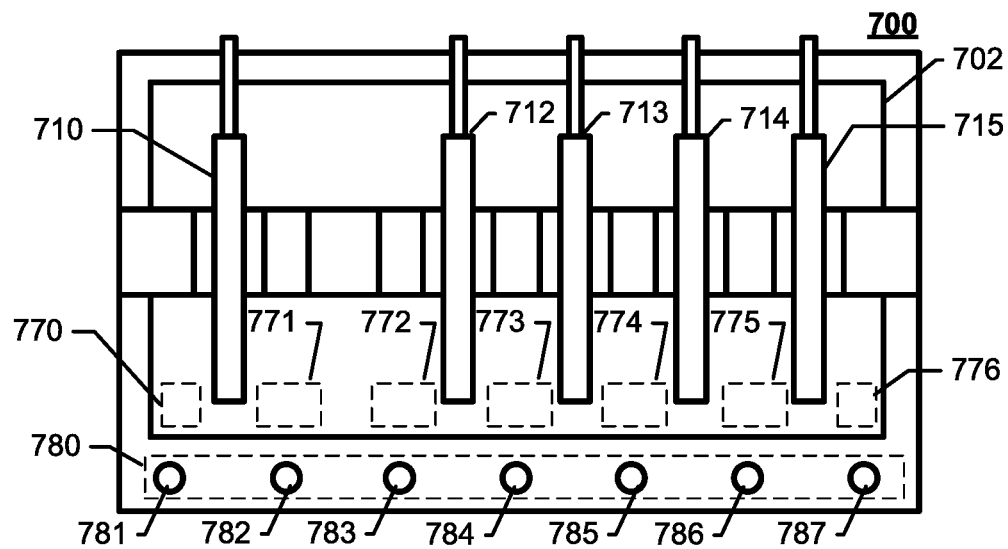

FIGS. 7*a-b* show a dental instrument bridge 700 according to an embodiment of the present invention. This embodiment is similar to the embodiment shown in FIG. 6 with the difference that the elongated input zone 780 comprises seven buttons 781-787. The seven buttons 781-787 may be proximity buttons configured to detect the presence of an object such as a finger of a user without any physical contact between the object and the proximity button and in response thereto generate an activation signal. The display 702 comprises seven button portions 770-776 one arranged above each of the seven buttons. The dental instrument bridge 700 is configured to control the display 702 to display information indicating the functionality of the buttons at their respective button portions of the display. FIG. 7*a* shows the dental instrument bridge 700, when no dental instruments are selected. In this state, the buttons 781-787 may be used to control general functions of a dental unit e.g. control a water tap, control light, or control the position of the dental chair. FIG. 7*b* shows the dental instrument bridge after the dental instrument 711 has been selected. The dental instrument bridge 700 will in response to the selection of the dental instrument 711 control the display 702 to change the current display and show first information relevant for the use of the dental instrument 711, and change the functionality of the seven buttons 781-787 so that they may be used to configure the dental instrument 711. As an example if the dental instrument 711 is a micro motor, the button 783 may be used for increasing the speed of the micro motor and the button 785 may be used for decreasing the speed of the micro motor as preferably indicated in the button portions 772 774 respectively.

Figure 8:
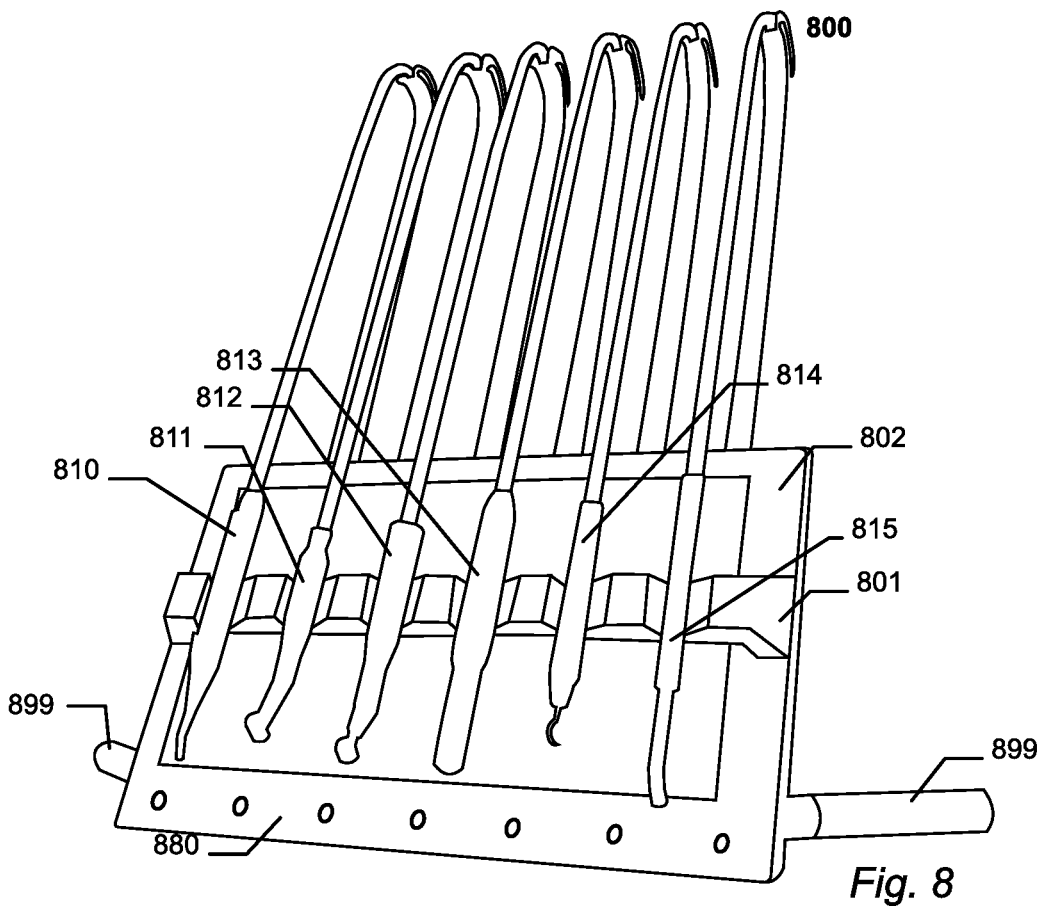
FIG. 8 shows a dental instrument bridge according to an embodiment of the present invention.

FIG. 8 shows a dental instrument bridge 800 according to an embodiment of the present invention. The dental instrument bridge 800 comprises: an instrument holder 801 configured to hold a plurality of dental instruments and a display 802 for displaying information related to a dental treatment. The instrument holder 801 comprises an elongated member extending along a central longitudinal axis and the display 802 comprises a first elongated part arranged above the elongated member of the instrument holder 801 and a second elongated part arranged below the elongated member of the instrument holder 801. The elongated member of the instrument holder 801 comprises six concave portions, each concave portion holding a dental instrument 810-815. In this embodiment the dental instrument bridge 800 further comprises an input unit 880 for setting values of one or more control parameters for one or more of the dental instruments 810-815. In this embodiment the following dental instruments are arranged in the instrument holder, a syringe 810, a first micro motor 811, a second micro motor 812, an intraoral camera 813, a scaler 814, and a curing light 815.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:
1. A dental instrument bridge for holding a plurality of dental instruments, said dental instrument bridge comprising:
    an instrument holder configured to hold a plurality of dental instruments; and a display for displaying information related to a dental treatment;

wherein said display has a plurality of covered portions, each covered portion of said plurality of covered portions being at least partly covered by one of said plurality of dental instruments when said one of said plurality of dental instruments is arranged in said instrument holder;

wherein said dental instrument bridge is configured to detect when a user selects and picks up a selected dental instrument of said plurality of dental instruments and in response thereto is configured to control the display to change a current display and show information relevant for the use of said selected dental instrument; and wherein the information relevant for the use of said selected dental instrument is displayed at least partly inside said covered portion of said display that is at least partly covered by said selected dental instrument, when said selected dental instrument is arranged in said instrument holder.

2. A dental instrument bridge according to claim 1, wherein said display has an adjacent portion next to each of said plurality of covered portions wherein the display is configured to, for each of said adjacent portions, show information relevant for the use of their respective dental instrument.

3. A dental instrument bridge according to claim 2, wherein the information relevant for the use of their respective dental instrument is a visual indicator indicating to the user that a dental instrument should be used for a next step of a particular dental treatment.

4. A dental instrument bridge according to claim 1, wherein said instrument holder comprises an elongated member extending along a central longitudinal axis; and said display comprises a first elongated part extending along said central longitudinal axis below or above said elongated member of said instrument holder.

5. A dental instrument bridge according to claim 4, wherein said first elongated part extends along said central longitudinal axis below said elongated member of said instrument holder; and said display further comprises a second elongated part extending along said central longitudinal axis above said elongated member of said instrument holder.

6. A dental instrument bridge according to claim 1, wherein the dental instrument bridge further comprises a housing and a movable arm, said display is arranged in said housing and said movable arm is connected to said housing, wherein said movable arm is configured to allow a user to arrange said instrument bridge at a desired position with respect to a patient.

7. A dental instrument bridge according to claim 1, wherein:

said dental instrument bridge further comprises an input unit for controlling functionalities of dental equipment;

said instrument holder comprises an elongated member extending along a central longitudinal axis, said elongated member being configured to hold a first dental instrument, a second dental instrument and a third dental instrument at three approximately predetermined positions;

the display having a first covered portion, a second covered portion and a third covered portion, the first covered portion being at least partly covered when said first dental instrument is arranged in said instrument holder, the second covered portion being at least partly covered when said second instrument is arranged in said instrument holder, and said third covered portion being at least partly covered when said third dental instrument is arranged in said instrument holder; and said input unit comprises an elongated input zone configured to allow a user to control functionalities of dental equipment using an object such as a finger where said elongated input zone is arranged above or below said elongated member and has a width along said central longitudinal axis whereby a user may select any one of said first, second or third dental instruments with a first hand and directly with said first hand enter said elongated input zone without moving said first hand along said central longitudinal axis.

8. A dental instrument bridge according to claim 7, wherein the display has one or more input unit portions, wherein the dental instrument bridge is configured to control the display to show information indicating the functionality of the elongated input zone at the one or more input unit portions.

9. A dental instrument bridge according to claim 7, wherein said elongated input zone comprises at least three buttons for setting values of one or more control parameters for each of said first, second or third dental instrument.

10. A dental instrument bridge according to claim 9, wherein the centre of each of said at least three buttons are arranged with a distance along said central longitudinal axis to any one of said three covered portions of said display whereby the parts of the display arranged immediately above or below said buttons are freely visible also when all dental instruments are arranged in the instrument holder.

11. A dental instrument bridge according to claim 1, wherein said display has a planar display surface extending in a first reference plane being angled with respect to the horizontal plane with an angle between 10 and 90 degrees, between 25 and 90 degrees, or between 35 and 80 degrees.

12. A dental instrument bridge according to claim 1, wherein said display has a planar display surface extending in a first reference plane, the first dental instrument is an elongated dental instrument extending along a first central longitudinal axis, and the instrument holder being configured to hold the first dental instrument in a manner whereby the angle between the first central longitudinal axis and the first reference plane is less than 30, 20, or 10 degrees.

13. A dental instrument bridge according to claim 12, wherein the planar display surface of the display has a length along the first central longitudinal axis of at least 5 cm, 10 cm, or 15 cm.

14. A dental instrument bridge according to claim 12, wherein the planar display surface of the display has a length along the first central longitudinal axis of at least 25%, 50%, or 75% of the length of the first dental instrument along the first central longitudinal axis.

15. A dental instrument bridge according to claim 1, wherein said display has a planar display surface extending in a first reference plane, the plurality of dental instruments are elongated dental instruments extending along central longitudinal axes, the instrument holder being configured to hold the plurality of dental instruments in a manner whereby their central longitudinal axes are arranged a third reference plane, the angle between the third reference plane and the first reference plane is less than 30 degrees, 20 degrees or 10 degrees.

16. A dental instrument bridge according to claim 15, wherein the planar display surface of the display has a length along the central longitudinal axes of at least 25%, 50%, or 75% of the average length of the plurality of dental instruments along the central longitudinal axes.

17. A dental unit for dental treatments comprising:
a dental instrument bridge according to claim 1; and
a patient chair.

* * * * *